United States Patent [19]

Lin et al.

[11] Patent Number: 5,414,077
[45] Date of Patent: May 9, 1995

[54] NON-NUCLEOSIDE LINKERS FOR CONVENIENT ATTACHMENT OF LABELS TO OLIGONUCLEOTIDES USING STANDARD SYNTHETIC METHODS

[75] Inventors: Kuei-Ying Lin, Fremont; Mark Matteucci, Burlingame, both of Calif.

[73] Assignee: Gilead Sciences, Foster City, Calif.

[21] Appl. No.: 237,233

[22] Filed: May 2, 1994

Related U.S. Application Data

[63] Continuation of Ser. No. 594,147, Oct. 9, 1990, abandoned, which is a continuation-in-part of Ser. No. 482,943, Feb. 20, 1990, abandoned.

[51] Int. Cl.$^6$ ............................................. C07H 21/04
[52] U.S. Cl. ............................... 536/24.3; 536/25.32; 546/23; 435/6
[58] Field of Search ........................... 536/24.3, 25.32; 546/23; 435/6

[56] References Cited

U.S. PATENT DOCUMENTS

| | | | |
|---|---|---|---|
| 2,457,569 | 1/1949 | Letsinger et al. | 536/23.1 |
| 3,360,528 | 12/1967 | Ribca | 546/23 |
| 4,479,000 | 10/1984 | Rewcastle et al. | 546/23 |
| 4,603,125 | 7/1986 | Atwell et al. | 514/80 |
| 4,605,735 | 8/1986 | Miyoshi et al. | 536/24.3 |
| 4,707,440 | 11/1987 | Stavrianopolous | 435/6 |
| 4,828,979 | 9/1989 | Klevan et al. | 435/6 |
| 4,904,582 | 2/1990 | Tullis | 435/6 |
| 4,910,300 | 3/1990 | Urdea et al. | 536/25.32 |
| 4,958,013 | 9/1990 | Letsinger | 536/24.3 |
| 5,124,246 | 6/1992 | Urdea et al. | 435/6 |

FOREIGN PATENT DOCUMENTS

| | | | |
|---|---|---|---|
| 0073155 | 3/1983 | European Pat. Off. | 546/23 |
| 9093096 | 5/1984 | Japan | 536/26.8 |
| 8905358 | 6/1989 | WIPO | 514/44 |

OTHER PUBLICATIONS van der Krol et al., "Modulation of Eukaryotic Gene Expression by Complementary RNA and DNA Sequences," *Biotechniques*, 6(10), 958–976 (1988).
Stein et al.(I), "Oligodeoxynucleotides as Inhibitors for Gene Expression: A Review," *Cancer Res.*, 48, 2659–2668 (1988).

(List continued on next page.)

*Primary Examiner*—Douglas W. Robinson
*Assistant Examiner*—L. Eric Crane
*Attorney, Agent, or Firm*—Morrison & Foerster

[57] ABSTRACT

Pseudonucleosides and pseudonucleotides are useful in the synthesis of oligomers which contain these components as a means to derivatize the resulting oligonucleotide to useful substituents such as chelators, intercalators, or lipophilic compounds. In general, these pseudonucleotide components are of the formula:

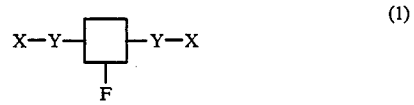

wherein each Y is independently O or S;

each X is independently H, $PO_3{}^{-2}$, an activated nucleotide synthesis coupling moiety, a protecting group, a nucleoside, a nucleotide or a nucleotide sequence, or comprises a solid support;

F is a functional group capable of linking an additional moiety or said group already reacted to effect the binding of said additional moiety;

□ is an organic backbone which does not contain additional F or Y-X substituents and which is either achiral even when the Y-X substituents are different, or is a single enantiomer of a chiral compound;

with the proviso that at least one X is a nucleoside, nucleotide, nucleotide sequence, an activated nucleotide synthesis coupling moiety, or comprises a solid support, or F represents said functional group already reacted with an additional group. Oligonucleotides having the pseudonucleoside at the 3' terminus are particularly stable in vivo.

9 Claims, No Drawings

OTHER PUBLICATIONS

Ogilvie et al., "Developments in Chemical Synthesis of Naturally Occurring DNA and RNA Sequences with Normal and Unusual Linkages," *Pure & Applied Chem.*, 59(3), 325–330 (1987).

Froehler et al., "Synthesis of DNA Via Deoxynucleoside H-Phosphonates," *Nucleic Acids Res.*, 14(13), 5399–5407 (1986).

Asseline et al.(I), "Solid-Phase Synthesis of Modified Oligodeoxyribonucleotides with an Acridine Derivative or a Thiophosphate Group at Their 3'-End," *Tetrahedron Lett.*, 30(19), 2521–2524 (1989).

Bayard et al., "Activation of Ribonuclease L by (2'-5')(A)$_4$-Poly(L-Lysine) Conjugates in Intact Cells," *Biochemistry*, 25(12), 3730–3736 (1986).

Lemaitre et al., "Biological Activities of Oligonucleotides Linked to Poly(L-Lysine)," *Nucleosides & Nucleotides*, 61(1&2), 311–315 (1987).

Zuckerman et al., "Efficient Methods for Attachment of Thiol Specific Probes to the 3'-Ends of Synthetic Oligodeoxynucleotides," *Nucleic Acids Res.*, 15(13), 5305–5321 (1987).

Lancelot et al., "Proton and Phosphorus Nuclear Magnetic Resonance Studies of an Oligothymidylate Covalently Linked to an Acridine Derivative and of Its Binding to Complementary Sequences," *Biochemistry*, 24(10), 2521–2529 (1985).

Asseline et al.(II), "Nucleic Acid-Binding Molecules with High Affinity and Base Sequence Specificity: Intercalating Agents Covalently Linked to Oligodeoxynucleotides," *Proc. Natl. Acad. Sci USA*, 81, 3297–3301 (1984).

Nelson et al.(I), "A New and Versatile Reagent for Incorporating Multiple Primary Aliphatic Amines into Synthetic Oligonucleotides," *Nucleic Acids Res.*, 17(18), 7179–7186 (1989).

Nelson et al. (II), "Bifunctional Oligonucleotide Probes Synthesized Using a Novel CPG Support Are Able to Detect Single Base Pair Mutations," *Nucleic Acids Res.*, 17(18), 7187–7194 (1989).

Letsinger et al.(II), "Effects of Pendant Groups at Phosphorus on Binding Properties of d-ApA Analogues," *Nucleic Acids Res.*, 14(8), 3487–3499 (1986).

Stein et al. (II), "Physicochemical Properties of Phosphorothioate Oligodeoxynucleotides," *Nucleic Acids Res.*, 16(8), 3209–3221 (1988).

Agrawal et al., "Oligodeoxynucleoside Methylphosphonates: Synthesis and Enzymatic Degradation," *Tetrahedron Lett.*, 28(31), 3539–3542 (1987).

Froehler, "Exonuclease-Resistant Oligonucleotides and Methods for Preparing the Same," U.S. patent application Ser. No. 07/361,045, filing date Jun. 5, 1989.

Matteucci, "Deoxyoligonucleotide Analogs Based on For macetal Linkages," *Tetrahedron Lett.*, 31(1), 2385–2388 (1990).

Buhr, "2'-Modified Oligonucleotides," U.S. patent application Ser. No. 07/425,857, filing date Oct. 24, 1989.

Haralambidis et al.(I), "The Solid Phase Synthesis of Oligonucleotides Containing a 3'-Peptide Moiety," *Tetrahedron Lett.*, 28(43), 5199–5202 (1987).

Haralambidis et al.(II), "The Synthesis of Polyamide–Oligonucleotide Conjugate Molecules," *Nucleic Acids Res.*, 18(3), 493–499 (1990).

Miller et al., "Biochemical And Biological Effects of Nonionic Nucleic Acid Methylphosphonates," *Biochemistry*, 20(7), 1874–1880 (1981).

Letsinger et al. (III), "Cholesteryl-Conjugated Oligonucleotides: Synthesis, Properties, and Activity as Inhibitors of Replication of Human Immunodeficiency Virus in Cell Culture," *Proc. Natl. Acad. Sci. USA*, 86, 6553–6556 (1989).

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CCCTCTCTTT TTCC         14

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TCCAGTGATT         10

( 2 ) INFORMATION FOR SEQ ID NO:3:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TTTTTCTCCA T         11

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

TCCCTCTCTT TTTCC         15

( 2 ) INFORMATION FOR SEQ ID NO:5:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear (x i) SEQUENCE DESCRIPTION: SEQ ID NO:5:

CCCTCTTTTT TTCC                                                                                   14

(2) INFORMATION FOR SEQ ID NO:6:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (x i) SEQUENCE DESCRIPTION: SEQ ID NO:6:

CCCTCTCTTT TTCT                                                                                   14

NON-NUCLEOSIDE LINKERS FOR CONVENIENT ATTACHMENT OF LABELS TO OLIGONUCLEOTIDES USING STANDARD SYNTHETIC METHODS

This application is a continuation, of application Ser. No. 07/594,147, filed 9 Oct. 1990, now abandoned, which is a continuation-in-part of U.S. Ser. No. 07/482,943, filed 20 Feb. 1990, now abandoned.

TECHNICAL FIELD

The invention relates to the incorporation into oligomers of pseudonucleosides/pseudonucleotides which can be employed as a means to conjugate useful substituents such as lipophilic groups, intercalators, and chelators, and which can confer desirable properties, including resistance to nucleases, enhanced specific binding to DNA or RNA targets, permeation into cells, and resistance to renal clearance. More specifically, the invention concerns incorporation of a dihydroxy-derived monomer which bears a functional group capable of conjugating useful moieties in place of a conventional nucleotide in oligomer synthesis. In addition, it is clear that extensive modifications at the 3' terminus can be made which enhance in vivo stability to exonucleases and which do not interfere with activity. The oligomers are useful in diagnosis.

BACKGROUND ART

The general principles of what was originally termed "antisense" therapy are now well recognized. Most diseases and undesirable conditions in humans and animal subjects are mediated by specific DNA or RNA sequences which, if inactivated, would no longer be able to facilitate the progress of the disease. The "antisense" approach provides DNA or RNA oligomers, or their analogs, which are capable of specific binding to the undesirable nucleic acid sequences; recently the possibility of specific binding of oligomers to protein targets has also been explored. These materials can be supplied directly or generated in situ, and may be conventional oligomers, or are more commonly oligomers having properties which make them, for example, resistant to nucleases or more capable of specific binding to the desired target. The specific binding may be effected by providing oligomers having sequences which result in conventional base-pairing, or these may recognize double-stranded DNA by binding to the major or minor grooves which are present in the double helix, or the oligomers, in either single stranded or duplex form may recognize target protein. Whatever the ultimate strategy, it is desirable to provide oligomers with physiological properties which render them more effective. Hence, the concept has expanded beyond a simple "antisense" approach to include any therapy by oligonucleotides. The general approach to constructing various oligomers useful in antisense therapy has been reviewed by vander Krol, A. R., et al., *Biotechniques* (1988) 6:958–976, and by Stein, C. A., et al., *Cancer Res* (1988) 48:2659–2668, both incorporated herein by reference.

The art provides a number of approaches whereby modified oligonucleotides are used in these expanded antisense applications. For example, in order to provide enhanced stability in vivo, through resistance to endogenous nucleases, oligomers have been synthesized with alternative linkages other than the conventional phosphodiester linkage. Among these are the methylphosphonates wherein one of the phosphorous-linked oxygens has been replaced by methyl; phosphorothioates, wherein sulfur replaces one of the oxygens; and various amidates, wherein $NH_2$ or organic amine derivatives, such as morpholidates or piperazidates, replace an oxygen. Also carbonate and carbamate linkages have been employed, as well as those involving sulfur rather than oxygen as a linking substituent.

In addition, modifications have been employed wherein the oligonucleotides are conjugated with a lipophilic group to enhance cell permeation capability. Inclusion of intercalators and chelators which enhance the ability of the oligonucleotide to bind the target DNA or RNA is also known. These substituents have been attached to the 5' end of preconstructed oligonucleotides using amidite or H-phosphonate chemistry, as described by Ogilvie, K. K., et al., *Pure and Appl Chem* (1987) 59:325, and by Froehler, B. C., *Nucleic Acids Res* (1986) 14:5399. Intercalators have also been attached to the 3' end of oligomers, as described by Asseline, U., et al., *Tet Lett* (1989) 30:2521. This last method utilizes 2,2'-dithioethanol attached to a solid support to displace diisopropylamine from a 3' phosphonate bearing the acridine moiety and is subsequently deleted after oxidation of the phosphorus. Other substituents have been bound to the 3' end of oligomers by alternate methods, including polylysine (Bayard, B., et al., *Biochemistry* (1986) 25:3730; Lemaitre, M., et al., *Nucleosides and Nucleotides* (1987) 6:311) and, in addition, disulfides have been used to attach various groups to the 3' terminus, as described by Zuckerman, R., et al., *Nucleic Acids Res* (1987) 15:5305. It is known that oligonucleotides which are substituted at the 3' end show increased stability and increased resistance to degradation by exonucieases (Lancelot, G., et al., *Biochemistry* (1985) 24:2521; Asseline, U., et al., *Proc Natl Acad Sci USA* (1984) 81:3297).

Recently, two papers have suggested the use of amino protected derivatives of 3-amino-1,2-propanediol for the insertion of an amino group capable of further derivatization to desirable labeling or other moieties. Nelson, P.S., et al., *Nucleic Acids Res* (1989) 17:7187–7194, describe the conjugation of the diol to a modified form of controlled pore glass, linked through the intermediation of succinic anhydride, wherein the resulting controlled pore glass is used as a synthesis support to obtain an oligonucleotide containing, ultimately, a reactive amino group at the 3' terminus. This technique permits double labeling of the oligonucleotide at both 3' and 5' ends wherein the 5' terminus is labeled by other means. In another report, Nelson, P.S., et al., *Nucleic Acids Res* (1989) 17:7179–7186, describe the incorporation of the protected cyanoethoxydiisopropyl aminophosphenyl derivative of 3-amino-1,2-propanediol into the nucleotide chain. This provides a free amino group at any location for subsequent derivatization. In this report, the amino-modified oligonucleotide was subsequently labeled with biotin. These constructions result in a chiral center and create a mixture of diastereomers.

The phosphodiester linkages of native DNA and RNA molecules are readily degraded by exonucleases present in cells, tissue culture media, serum, blood and other body fluids. For example, exonuclease activity in tissue culture media containing serum results in extensive DNA or RNA oligomer degradation within about 30 minutes to 6 hours. Synthetic oligodeoxynucleotides with conventional phosphodiester linkages can be readily used in genetic engineering, for example, to locate specific RNA or DNA fragments from a library, since these oligonucleotides are usually not exposed to the relatively stringent environment of the culture medium; however, therapeutic uses in humans or animals and research applications in tissue culture require nucleic acid molecules that are stable under these conditions for more than several hours or days.

For example, oligonucleotides can be used to block protein synthesis by hydrogen bonding to complementary messenger RNA (mRNA) thereby providing a therapeutic agent for use in an antisense mode. Exonuclease-stable oligonucleotides could also be utilized to form triple-helix nucleic acid complexes which would interfere with the transcription process or with DNA replication by competing with naturally occurring binding factors or polymerases, or by irreversible gene inactivation. In order to utilize synthetic oligonucleotides in this manner, they must be stable to intracellular and extracellular exonucleases.

The major exonuclease activity associated with cells and body fluids appears to progress 3' to 5' on the substrate oligonucleotide. Although exonucleases which progress from the 5' to 3' termini of the substrate oligonucleotide are detectable in cell culture media under tissue culture conditions, this type of degradation appears to play a smaller role in vivo in whole organisms, as described in the parent application, Ser. No. 07/482,943.

Much research has been devoted to the synthesis of oligonucleotides that are nuclease-stable. This work has centered on modification of internucleotide phosphodiester linkages in order to render the linkage resistant to enzyme-mediated hydrolytic attack. As expected, modified internucleotide linkages are generally nuclease resistant. For example, Miller et al., *Biochemistry* (1981) 20:1874–1880, describe the synthesis and properties of oligodeoxyribonucleoside methylphosphonates, which oligomers were shown to be resistant to nuclease activity in vivo. Letsinger et al., *Nucleic Acids Res* (1986) 14:3487–3499, describe hydrogen bonding to complementary sequences and nuclease stability properties of short oligomers (dimers and trimers) possessing pendant groups linked to the oligomer at internucleotide phosphodiester linkages. These modified phosphodiester linkages were shown to be resistant to individual endo- and exonucleases compared to unmodified linkages under in vitro conditions. Stein et al., *Nucleic Acids Res* (1988) 16:3209–3221, describe the nuclease resistance properties of oligodeoxynucleotides modified to contain phosphorothioate internucleotide linkages. Although the phosphorothioate compounds were stable in vitro to individual nucleases, the binding affinity to complementary nucleic acid sequences was significantly reduced. Agrawal et al., Tet Lett (1987) 28:3539–3542, show enhanced endonuclease and exonuclease stability for oligodeoxynucleotides containing methyl-phosphonate-modified internucleotide linkages under in vitro conditions.

Walder et al., PCT publication WO89/5358, describe oligonucleotides modified at the 3' terminal internucleotide linkage that are more stable than control compounds with unmodified phosphodiester linkages. Copending application U.S. Ser. No. 07/361,045, assigned to the same assignee, describes oligonucleotides containing phosphoramidate linkages at the 3' terminal linkages which are stable to nucleases under both intracellular and extracellular conditions. Matteucci, *Tet Lett,* (1990) 37:2385–2388, describes the synthesis and properties of oligodeoxynucleotides containing formacetal internucleotide linkages which are exonuclease stable under in vitro conditions.

In the foregoing reports, nuclease stability results from modification of internucleotide linkages. In other instances, nuclease stability was obtained through alternate modifications. Copending application U.S. Ser. No. 07/425,857, by Buhr and Matteucci, describes by modification of the 2' hydroxyl positions of the oligomers. Haralambidis et al., *Tet Lett* (1987) 28:5199–5202, describe the attachment of a peptide to the 3' hydroxyl terminus of an oligonucleotide which was resistant to a 3' exonuclease (snake venom phosphodiesterase) under in vitro conditions. Further analysis of these oligonucleotide-peptide conjugates by Haralambidis et al., *Nucleic Acids Res* (1990) 18:493–499, showed they were, however, sensitive to P1 3' exonuclease. In none of these studies was stability of the compounds to serum or intracellular conditions (the conditions pertinent to stability for in vivo therapeutic use) tested, although it is known generally that modifications at the 3' terminus offer enhanced stability (supra).

The present invention provides modified oligonucleotides which bear useful substituents at the 3' or 5' end, or at any intermediate position, by virtue of inclusion of at least one pseudonucleoside unit in the construction of the polymer, which, in turn provides a means for conjugation of desirable substituents such as intercalators, lipophilic groups, or chelators, in addition the invention provides additional 3' modified oligomers with enhanced nuclease resistance.

DISCLOSURE OF THE INVENTION

The invention is directed to monomers useful to construct DNA or RNA oligomers which can be employed in diagnosis through binding to specific target oligonucleotides. The invention compounds are pseudonucleosides or pseudonucleotides which are intermediates in the synthesis of modified oligomers, as well as the resulting modified oligomers per se. Because the pseudonucleotide provides a functional group for the conjugation of any desired substituent, the resulting oligomers can be modified as desired to exhibit such helpful properties as resistance to nucleases, enhanced binding to target sequences, enhanced capability to permeate cells, and regulation of the rate of renal clearance.

Accordingly, in one aspect, the invention is directed to compounds of the formula:

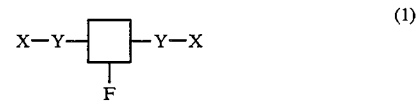

(1)

wherein each Y is independently O or S;
each X is independently H, $PO_3^{-2}$, an activated nucleotide synthesis coupling moiety, a protecting group, a nucleoside, a nucleotide or a nucleotide sequence, or comprises a solid support;
F is a functional group capable of linking an additional moiety or said group already reacted to effect the binding of said additional moiety;
□ is an organic backbone which does not contain additional F or Y-X substituents and which is either achiral even when the Y-X substituents are different, or is a single enantiomer of a chiral compound; with the proviso that at least one X is a nucleoside, nucleotide, nucleotide sequence, an activated nucleotide synthesis coupling moiety, or comprises a solid support, or F represents said functional group already reacted with an additional group selected from a chelator, intercalator, reporter group, cleavage entity, crosslinker, and a protecting group.

The present invention is also directed to oligonucleotides that are exonuclease stable under both in vivo and in vitro conditions due to modifications at the 3' terminal nucleotide including conjugation at the 3' hydroxyl position. These oligonucleotides are highly nuclease stable under tissue culture conditions where numerous characterized and uncharacterized nuclease activities occur. The nuclease stability of the invention compounds permits their application in nuclease-rich conditions such as blood or serum with substantial undegraded compound remaining after 3 days in tissue culture or in cells.

In other aspects, the invention is directed to methods to synthesize the oligomers of the invention which contain the pseudonucleotide residues described above, and to methods to employ the resulting oligomers in diagnosis.

MODES OF CARRYING OUT THE INVENTION

A. Definitions

"Oligomers" or "oligonucleotides" includes sequences of more than one nucleotide in either single chain or duplex form and specifically includes short sequences such as dimers and trimers, in either single chain or duplex form.

The oligonucleotides in which the pseudonucleotides are included may be conventional DNA or RNA moieties, or may be "modified" oligomers which are those conventionally recognized in the art. For example, any of the hydroxyl groups ordinarily present may be replaced by phosphonate groups, phosphate groups, protected by standard protecting group, or activated to prepare additional linkages to additional nucleotides, or may be conjugated to solid supports. The 5' terminal OH is conventionally phosphorylated; any 2'-OH or OH substituents at the 3' terminus may also be phosphorylated. The hydroxyls may also be derivatized to standard protecting groups. The phosphodiester linkage shown may be replaced by alternative linking groups. These alternative linking groups include, but are not limited to embodiments wherein P(O)O is replaced by P(O)S, P(O)NR$_2$, P(O)R, P(O)OR', CO, or CNR$_2$ wherein R is H or alkyl (1–6 C) and R' is alkyl (1–6 C); in addition, this group may be attached to adjacent nucleotide through O or S. Not all linkages in the same oligomer need to be identical.

In this regard, one possible embodiment for X in the compound of formula 1 is that of an "activated nucleotide synthesis coupling moiety." By this phrase is meant the array of phosphorous-containing groups which are used as intermediates in standard oligonucleotide synthesis either in the formation, ultimately, of phosphodiester linkages or the alternate linkages noted above.

"Analogous" forms of purines and pyrimidines are those generally known in the art, many of which are used as chemotherapeutic agents. An exemplary but not exhaustive list includes 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'methoxycarbonylmethyluracil, 5-methoxyuracil, 2-methylthio-N6-isopentenyladenine, uracil-5-oxyacetic acid methylester, uracil-5-oxyacetic acid (v), wybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid (v), pseudouracil, queosine, 2-thiocytosine, and 2,6-diaminopurine.

The invention is directed to new compounds which are useful as defined above and intermediates in their production, as well to methods to synthesize these compounds and their intermediates. The oligomers include at least one pseudonucleotide, which can be positioned at the 3' or 5' terminus, or can be at any intermediate position in the oligomer.

Substitution at the 3' terminus results in enhanced in vivo stability. The viability of oligomers having a pseudonucleotide at the 3' terminus demonstrates the scope of modification which can be tolerated at this position. It is thus apparent that a 3' substitution on the sugar or base will enhance stability in vivo while permitting the oligomer to retain its activity.

To the extent that the remaining sequence of the oligomer is conventional, it can be represented in conventional notation, as in standard DNA (or RNA) sequences noted by the sequence of bases alone, such as, for example, ATG CGC TGA. Usually it is simply stated in advance whether this represents a DNA or RNA sequence. In the compounds of the invention, a similar notation will be used for modifications of otherwise physiological DNA or RNA molecules, but where the pseudonucleotide is inserted, this will be represented by inclusion of a "P" in place of the conventional residue; for example, 5'-ATG-P-GTCA-P-AGG-3, indicates an oligonucleotide wherein two residues are, in fact, pseudonucleotide residues. Where other modifications are made in the remaining nucleotide sequence attached to the pseudonucleotide, a more definitive system of notation must be used. For example, it may be possible to denote the remaining nucleotide portions using the system:

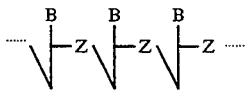

wherein each B is independently a conventional or analogous base and each Z represents a conventional phosphodiester or alternate linkage.

It should also be noted that while a primary function of the pseudonucleotide inclusion is to permit the conjugation of additional moieties to the oligomer to improve its properties, it is not excluded to include in the additional nucleotide sequence substituents conjugated using other known techniques, such as those coupled through any available OH or SH moiety, for example, at the 5' position of RNA or DNA, the 2' position of RNA, or an NH$_2$ or SH engineered into the 5 position of pyrimidines.

In the compound of formula (1), the organic backbone is either achiral even when the two Y-X substituents differ, or represents a single enantiomer of a chiral compound, so that multiple products are not obtained when the pseudonucleotide of formula (1) is included in the oligomer. A suitable achiral backbone is provided, for example, by the carbon skeleton to diethanolamine of the formula HOCH$_2$CH$_2$NHCH$_2$CH$_2$OH. Additional homologs of the general formula HY(CH$_2$)$_n$NH(CH$_2$)$_n$YH, wherein n is 1–10 may also be used. In this embodiment, each Y-X is OH or SH, and the functional group F is provided by the amino functionality NH. As is seen, the organic backbone is not necessarily contiguous but is achiral and is devoid of additional functional groups which would interfere with the inclusion of this pseudonucleoside in an oligomer. The NH functionality is readily conjugated to additional substituents.

A slightly modified form of the pseudonucleoside results from the substitution of an alkylene diamine for the ammonia centerpiece of the diethanolamine and its homologs. These compounds are of the formula

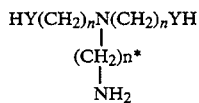

wherein n* is 1–10, preferably 2–4. In these pseudonucleosides, a primary amine functional group is substituted for the secondary amine of diethanolamine and its analogs. The form of these pseudonucleosides wherein a secondary amine is a functional group is obtained by alkylating the primary amino group with an alkyl of 1–6 C, for example.

An additional example of the nature of the organic backbone of the compound of formula (1) is represented by:

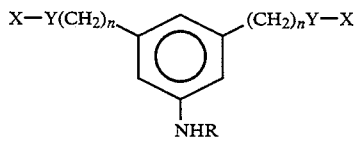

wherein n is 0–5, R is H or alkyl (1–6 C) and wherein again the amino moiety provides a suitable linking group. The organic backbone in this case is contiguous.

It should be noted that the compound of formula (1) is not only achiral per se when both Y-X are the same, but does not become chiral when one of these substituents is derivatized. That is, even when both Y-X substituents are not the same, achirality is maintained. In the diethanolamine embodiment, this is possible because N does not provide a chiral center; in the substituted benzene, the benzene ring provides a nonchiral focus.

Although compounds of formula (1) which are achiral are advantageous in resulting in a uniform product, chiral compounds can also be used if they can be provided unambiguously as a single enantiomer where derivatization can be conducted preferentially at one position. Suitable candidates are, for example, derived from amino acid residues which can be isolated as single enantiomers wherein the carboxyl group is replaced by hydroxyl or SH. For example, reduced forms of serine, cysteine, or threonine may be used, as well as hydroxylated or keto acids from the citric acid cycle. However, large quantities of achiral and non-prochiral compounds are equally useful and are more convenient to obtain.

Suitable functional groups for binding additional moieties include amino groups, since nitrogen also forms a convenient point of resistance to chirality, but where, for example, organic backbones relying on benzene as an achiral center or the enantiomers derived from natural products are employed, any convenient conjugating functional group can be used, including SH, carboxyl, CHO, and the like. In general, it is preferred, but not required, that the functional group be derivatized to the desired substituent before inclusion in the oligonucleotide so that competing reactions with, for example, substituents on the purine and pyrimidine bases are avoided.

Substituents to be conjugated to the compounds of formula (1) include lipophilic groups such as steroids, e.g., cholesterol; intercalators such as acridine and anthraquinone; and chelators such as EDTA. Also useful are fluorescent or radioisotopic labels when the oligomer is to be used as a probe.

In more detail, these substituents can include:

1) Reporter groups, such as fluorescent tags, e.g., fluorescein, rhodamine, phenanthroline metal complex; and/or radioisotopes, e.g., $^{125}$I-labeled tyrosine, $^{14}$C-labeled acetate, and $^{35}$S-labeled methionine.

2) Cleavage entities such as chelator ligands for transition metals capable of oxygen-mediated redox chemistry; e.g., copper phenanthroline, iron EDTA, iron porphyrin.

3) Moieties to confer membrane penetration, including, but not limited to, lipophilic groups such as steroids, e.g., cholesterol or other aids to permeation such as poly-or oligolysine.

4) Small molecules that have known DNA- or RNA-binding activities, such as intercalators; e.g., acridines or anthraquinones.

5) DNA cross-linking agents, such as psoralen, nitrogen mustards, aziridines, or alkyl halides.

6) Protected functional groups that can be derivatized after automated machine synthesis is complete, such as amino groups protected as trifluoroacetyl amides or FMOC carbamates; thiol groups protected as benzoyl thioesters or S-trityls.

The nature of the -Y-X group depends, in large part, on the status of the compound of formula (1) in the course of the construction of an oligomer. In its simplest form, the compound of formula (1) is a dihydroxy compound or a disulfhydryl compound or a monosulfhydryl monohydroxyl compound—i.e., a pseudonucleoside. However, in the course of synthesis of an oligomer which includes the pseudonucleoside, one of the hydrogens may advantageously be replaced by a protecting group such as dimethoxytrityl (DMT). In the course of oligomer synthesis, also, one hydrogen may advantageously be removed and the pseudonucleoside linked to a solid support, for example, as conventionally effected through succinic anhydride. In addition, if used in other than the 3'-terminal position, the pseudonucleoside will be derivatized as the phosphonate or phosphoramidate or phosphate. Finally, when contained in the oligomer, either or both X moieties will be nucleotide or modified nucleotide sequences.

The pseudonucleosides/pseudonucleotides of the invention and the oligomers which contain them may thus be capable of forming salts. Most commonly these entities are anions at neutral pH, and may thus be supplied or formulated as the salts, preferably of pharmaceutically acceptable cations, including metal ions such as potassium, sodium, calcium, magnesium or ammonium, or organic cations such as choline, caffeine or procaine.

B. Synthesis

The pseudonucleosides or pseudonucleotides of the invention can be included in an oligomer using standard solid phase synthesis techniques, for example, using H-phosphonate chemistry, as described by Froehler, B., et al., *Nucleic Acids Res* (1986) 14:5399, or by the methods of Matteucci, M., et al., *J Am Chem Soc* (1981) 103:3185. In these approaches, the growing nucleotide chain is attached to solid support such as controlled-pore glass (CPG) and extended from the 3' terminus one nucleotide at a time using a nucleotide protected in the 5' position; followed by deprotection and addition of a subsequent nucleotide residue. The pseudonucleosides can be modified and employed in this synthesis in a manner completely analogous to that described for conventional synthesis.

When the constructed oligonucleotide is derivatized through the pseudonucleoside or pseudonucleotide residue, optimization of the synthesis can be effected by derivatizing the additional material to the pseudonucleotide before or after its inclusion in the oligomer. If the moiety to be added is capable of being attached to the pseudonucleotide linker under sufficiently mild conditions that degradation of the oligonucleotide is avoided, it is convenient to couple this moiety after the oligonucleotide synthesis is completed. If this is done, the functional group on the pseudonucleotide or pseudonucleoside may need to be protected. A suitable protecting group, illustrated below, is trifluoroacetyl. The protecting group is in place during the oligonucleotide synthesis and decoupling from the solid support, and then removed to permit coupling to the additional moiety. For example, fluorescein and rhodamine can be prepared as reactive moieties which readily couple to an amino nitrogen in the pseudonucleotide residue. On the other hand, acridine and anthraquinone are generally coupled to a corresponding amino nitrogen under somewhat harsher conditions, and it is preferable to use the already derivatized pseudonucleotide in the synthesis. These practices are followed in the examples below. Such optimization procedures are well within the ordinary skill of the chemical practitioner who would routinely review the nature of the coupling reaction between the moiety to be attached to the functional group of the pseudonucleotide and the conditions under which coupling would best occur.

In particular, the pseudonucleosides or pseudonucleotides must be protected or derivatized at their functional groups during oligonucleotide synthesis. Therefore, if the pseudonucleoside residue is to be derivatized after the coupling to form the oligomer or if an underivatized pseudonucleotide is to be present in the final oligomer, the protected forms are used during the oligonucleotide synthesis.

C. Utility and Administration

Accordingly, the modified oligomers of the invention are useful in diagnostic and research contexts.

In addition, the oligomers of the invention may be used as diagnostic reagents to detect the presence or absence of the target DNA or RNA sequences to which they specifically bind. Such diagnostic tests are conducted by hybridization through base complementarity or triple helix formation which is then detected by conventional means. For example, the oligomers may be labeled using radioactive, fluorescent, or chromogenic labels and the presence of label bound to solid support detected. Alternatively, the presence of a double or triple helix may be detected by antibodies which specifically recognize these forms. Means for conducting assays using such oligomers as probes are generally known.

In general, the utilization of the pseudonucleotides at the 3'-terminus of the oligomers which include them greatly enhance the stability of these compounds to nucleases found under in vivo conditions. The ability to substitute for an entire nucleotide the pseudonucleotide structure in this position indicates that major modifications can be made to the commonly found 3'-terminal nucleotides, including modifications at the 3'hydroxyl (and 2' hydroxyl) of the 3'-terminal nucleotide in RNA) or at the base residue at this nucleotide position.

The following examples are intended to illustrate, but not to limit, the invention.

EXAMPLE 1

Preparation of Derivatized Diethanolamine (DEA) and Dihydroxyethyl ethylene diamine (DHED) Pseudonucleosides

A. An Acridine DEA: 6-chloro-9-[(N,N-di-2-ethanolamino)ethyl]amino-2-methoxyacridine 6,9-dichloro-2-methoxyacridine (3.6g; 12.9 mmol), N,N-bis(2-hydroxyethyl)ethylenediamine (2.1 g; 14.5 mmol), and phenol (7 g) were heated at 110° C. for an hour. The reaction mixture was then cooled to room temperature, diluted with methanol (30 ml), then triturated with saturated sodium bicarbonate (50 ml). The yellow precipitate was filtered off, washed thoroughly with water, acetone, and ether, and dried under vacuum overnight. The yield of the title compound was 4.70 g, 94%.

B. A Cholesterol DEA: Cholesteryl N,N-diethanol carbamate

Cold (0° C.) methylene chloride solution (15 ml) of cholestryl chloroformate (0.9 g, 2 mmol) was added slowly to cold (0° C.) diethanolamine (0.52 g; 10 mmol) in methylene chloride (10 ml) and pyridine (2 ml). After one hour reaction at 0° C. the reaction mixture was washed with saturated sodium bicarbonate aqueous solution (20 ml). The organic solution was isolated, dried over $Na_2SO_4$, and concentrated. The residue was applied on a silica gel flash column chromatography to give the title compound, 0.55 g, 55%.

C. An Anthraquinone DEA: 2-(N,N-diethanolamino) anthraquinone

A mixture of 2-chloroanthraquinone (2.42 g; 10 nmole) and an excess of diethanolamine in DMSO (20 ml) was heated to 150° C. After 24 hours reaction, the reaction mixture was cooled to room temperature, then poured into water (70 ml). The red precipitate was filtered off, washed thoroughly with water, and dried in air. The crude product, containing some starting material, was used for the reaction of Example 2, paragraph C, without further purification.

D. Ethyl DEA: N-Ethyldiethanolamine

This compound is commercially available.

E. A Trifluoroacetyl Protected Form of Diethanolamine (TFA/DEA): N,N-bis (2-hydroxyethyl)trifluoroacetamide Diethanolamine (5.0 g; 34 mmol) was dissolved in methanol (20 ml) and treated with triethylamine (4.7 ml; 34 mmole) and ethyl trifluoroacetate (4.9 g; 34 mmole) at room temperature for 16 hours followed by addition of 1 ml of ethyl trifluoroacetate to the reaction. After an additional 16 hours, the reaction mixture was evaporated to dryness affording the title compound.

F. A Trifluroacetyl (TFA) Protected Form of the Pseudonucleoside N,N-bis-(2-hydroxyethyl)ethylenediamine (TFA/DHED): N,N-(bis-(2-hydroxyethyl) aminoethyl)trifluoroacetamide N,N-bis-(2-hydroxyethyl)ethylenediamine (3.0 g; 24 mmole) and ethyltrifluoroacetate (4.1 g; 29 mmole) were reacted at room temperature for 5 hours. Excess ethyltrifluoroacetate and ethanol by-product were evaporated to dryness affording quantitative yield of the title compound.

EXAMPLE 2

DMT Protection of the Pseudonucleosides

A. DMT Protection of the Acridine DEA

To a cold pyridine/triethylamine (60 ml/15 ml, 0° C.) solution of the compound prepared in Example 1, paragraph A, (4.7 g; 12.2 mmol) was added N,N-dimethylaminopyridine (DMAP, 0.3 g) and 4,4'-dimethoxytrityl chloride (DMT-Cl, 5.80 g; 17 mmol). The resulting mixture was allowed to warm to room temperature. After 3 hours reaction, the reaction mixture was concentrated to dryness. The residue was then partitioned between methylene chloride and saturated sodium bicarbonate. The organic phase was separated, washed with water, dried, and concentrated. The residue was purified by flash column chromatography on silica gel, eluted with 1% $Et_3N$-1%$CH_3OH$-$CH_2Cl_2$, to afford 5.40 g of the mono-DMT-protected 6-chloro-9-[(N,N-di-2-ethanolamino)ethyl]amino-2-methoxyacridine.

B. DMT Protection of the Cholesterol DEA

To a cold methylene chloride/triethyl amine (10 ml/1.5 ml; 0° C.) solution of the compound prepared in Example 1, paragraph B (0.48 g; 0.92 mmol) was added N,N-dimethylaminopyridine (DMAP) (20 mg) and 4,4'-dimethoxytrityl chloride (0.38 g; 1.11 mmol). After 2 hours of reaction at 0° C., the reaction mixture was washed with saturated sodium bicarbonate. The organic solution was separated, dried, concentrated, then purified by flash column chromatography on silica gel, eluted with 1% $Et_3N$/$CH_2Cl_2$, to give 0.345 g of the mono-DMT-protected cholesteryl N,N-diethanol carbamate.

C. DMT Protection of the Anthraquinone DEA

The crude compound prepared in Example 1, paragraph C, was dissolved in pyridine (20 ml) and triethyl amine (1.7 ml), cooled to 0° C., followed by addition of DMAP (0.2 g) and DMT-Cl (4.0 g; 12 mmol). The reaction mixture was warmed to room temperature. After 4 hours of reaction, more DMT-Cl (1 g) was added to the reaction mixture and reacted one more hour, then concentrated to dryness. The residue was then partitioned between methylene chloride and saturated sodium bicarbonate solution. The organic solution was separated and dried, purified by flash column chromatography on silica gel, eluted with 1% $Et_3N$/1% $CH_3OH$/$CH_2Cl_2$, to afford the product mono-DMT-protected 2-N,N-diethanolaminoanthraquinone, in an amount of 0.7 g (13% overall yield); 3.1 g of unreacted starting material was recovered.

D. DMT Protection of N-Ethyl DEA

A pyridine solution (50 ml) of N-ethyldiethanolamine (13.3 g; 0.1 mole), $Et_3N$ (3 ml), and DMAP (30 mg) was cooled to 0° C., followed by addition of DMT-Cl (6.65 g; 0.02 mole). After 3 hours at room temperature, the reaction was worked up as usual, purified by flash column chromatography on silica gel, and eluted with 1% $Et_3N$/$CH_2Cl_2$, 1% $Et_3N$/1%$CH_3OH$/$CH_2Cl_2$. The mono-DMT-protected N-ethyldiethanolamine, 5.66 g, was obtained as an oil.

E. DMT Protection of the TFA/DEA (N-2-hydroxyethyl-N-2-DMT-ethyl)trifluoroacetamide The TFA derivative prepared in Example 1, paragraph E (8.1 g; 34 mmole), was dissolved in 50 ml methylene chloride and 6.0 ml (43 mmole) of triethylamine and cooled to 0C. 4-(N,N-dimethylamino)-pyridine (DMAP; 50 mg) and 4,4'-dimethoxytrityl chloride (DMT-Cl, 13.8 g: 40.8 mmole) was added and the mixture was brought to room temperature and allowed to react for 2 hours, washed with 1 M TEAB aqueous solution twice, dried over $Na_2SO_4$ and evaporated to dryness. The residue was purified by flash column chromatography on silica gel, eluted with 1% $Et_3N$/1% methanol/methylene chloride, affording 3.3 g of product (18% yield).

F. DMT Protection of the TFA/DHED [N-(2-hydroxyethyl)-N-(2-DMT-ethyl)]aminoethyltrifluoroacetamide The ETFA derivative prepared in Example 1, paragraph F (5.8 g; 24 mmole), was dissolved in 50 ml methylene chloride and triethylamine (3.0 g; 29 mmole), cooled to 0° C. followed by addition of 50 mg DMAP and 9.75 g of DMT-Cl (28.8 mmole). The mixture was then reacted at room temperature for 2 hours and washed with 1 M TEAB aqueous solution twice. The methylene chloride was isolated, dried over $Na_2SO_4$ then evaporated to dryness. The residue was purified by flash column chromatography on silica gel, affording 4.17 g of product, 31.8% yield.

EXAMPLE 3

Conjugation to CPG Support

After succinylation as described for each pseudonucleoside below, 3-5 equivalents of the succinylated pseudonucleoside, 10 equivalents of diisopropylcarbodiimide, a catalytic amount of DMAP and CPG in DMF/pyridine (4/1; 4 ml/g CPG) were shaken at room temperature overnight and then capped with acetic anhydride and pyridine. After 4 hours capping at room temperature, quenching by slow addition of methanol, CPG was filtered off and washed thoroughly with methylene chloride, methanol, and ether, and dried under vacuum overnight. The resulting CPG derivatives with pseudonucleoside are then used to provide the pseudonucleoside at the 3' terminus of an oligonucleotide.

A. Succinylation of the Mono-DMT-Protected Acridine/DEA Pseudonucleoside

A pyridine solution (40 ml) of the DMT-protected acridine pseudonucleoside of Example 2, paragraph A, (5.4 g; 7.85 mmol), DMAP (0.3 g) and succinic anhydride (1.5 g; 15 mmol) was reacted at room temperature overnight and concentrated. The residue was then dissolved in methylene chloride, washed with 1M TEAB aqueous solution. The organic solution was isolated, dried over $Na_2SO_4$, concentrated, then purified by flash column chromatography, and eluted with 1% $Et_3N/2\%$ $CH_3OH/CH_2Cl_2$, 1% $Et_3N/5\%$ $CH_3OH/CH_2CH_2$, to afford the succinylated product (3.5 g, 56% yield).

B. Succinylation of the Mono-DMT-Protected Cholesteryl/DEA Pseudonucleoside

A mixture of the DMT-protected cholesteryl pseudonucleoside of Example 2, paragraph B (0.134 g; 0.18 mmol), DMAP (10 mg) and succinic anhydride (85 mg; 0,85 mmol) in pyridine (3 ml) was stirred at room temperature overnight. The reaction was worked up as described in Example 3, paragraph A, to give the succinylated form of the compound (0.125 g, 75%) as a white solid.

C. Succinylation of the Mono-DMT-Protected Anthraquinone/DEA Pseudonucleoside A mixture of the DMT-protected anthraquinone pseudonucleoside of Example 2, paragraph C (0.5 g; 0.81 mmol), DMAP (0.1 g) and succinic anhydride (0.326 g; 3.26 mmol) in pyridine (10 ml) was stirred at room temperature for 4 hours, and more succinic anhydride (0.1 g) was added to the reaction. After 2 more hours of reaction, the reaction was worked up as described in Example 3, paragraph A. The succinylated form of the subject compound (0.39 g) was isolated as a red solid (yield 59%).

D. Succinylation of the Mono-DMT-Protected Ethyl/DEA Pseudonucleoside

A mixture of the DMT-protected N-ethyldiethanol amine of Example 2, paragraph D (4.8 g; 11 mmol), DMAP (0.1 g) and succinic anhydride (2.2 g; 22 mmol) in pyridine (30 ml) was reacted at room temperature overnight. After workup, the succinylated form of the subject compound (0.39 g) was obtained as a brownish oil (58%).

E. Succinylation of the Mono-DMT-Protected TFA/DEA Pseudonucleoside

The DMT protected compound of Example 2, paragraph E (5.8 g; 24 mmole) was dissolved in 50 ml methylene chloride and triethylamine (3.0 g; 29 mmole), cooled to 0° C., followed by addition of 50 mg of DMAP and DMT-Cl (9.75 g; 28.8 mmole). The mixture was brought to room temperature and reacted for 2 hours and then washed with 1 M aqueous TEAB solution twice. The methylene chloride solution was isolated, dried over $Na_2SO_4$ and evaporated to dryness. The residue was purified by flash column chromatography on silica gel, affording 4.17 g of product, 31.8% yield.

F. Succinylation of the Mono-DMT-Protected TFA/DHED Pseudonucleoside

The DMA protected compound of Example 2, paragraph F (2.7 g; 4.9 mmole) was dissolved in 40 ml of acetonitrile containing TEA (1.5 g; 14.8 mmole) and 50 mg DMAP, then reacted with succinic anhydride (1.48 g; 14.8 mmole) for 2 hours at room temperature. The reaction mixture was evaporated to dryness, dissolved in methylene chloride, washed twice with 1 M TEAB aqueous solution, dried with $Na_2SO_4$ and concentrated to dryness. The residue was purified by flash column chromatography on silica gel, affording 3.10 g of product; 84% yield.

EXAMPLE 4

Phosphorylation of Mono-DMT-Protected Pseudonucleosides

A. Phosphorylated DMT-Protected Acridine DEA Pseudonucleoside

To a cold, stirring methylene chloride solution (30 ml; 0° C.) of 2-chloro-4H-1,2,3-benzodioxaphosphorin-4-one (2.4 ml of 1M methylene chloride solution; 2.4 mmol) and pyridine (0.2 g; 2.4 mmol) was added the DMT-protected pseudonucleoside of Example 2, paragraph A (0.55 g; 0.8 mmol). After stirring at 0° C. for 1 hour, the reaction mixture was poured into 1M TEAB aqueous solution (60 ml). The organic solution was separated, dried, concentrated. The residue was purified by flash column chromatography, eluted with 1% $Et_3N/CH_2Cl_2$, 1% $Et_3N/1\%CH_3OH/CH_2Cl_2$. The combined fraction of the product was washed with 1M TEAB aqueous solution, dried over $Na_2SO_4$, and concentrated, affording 0.19 g, 65% of the phosphorylated DMT-protected acridine pseudonucleotide.

B. Phospborylated DMT-Protected Anthraquinone DEA Pseudonucleoside

To a cold methylene chloride solution (8 ml; 0° C.) of the DMT-protected anthraquinone pseudonucleoside of Example 2, paragraph C (0.24 g; 0.39 mmol) were added pyridine (0.1 ml) and 2-chloro-4H-1,2,3-benzodioxaphosphorin-4-one (1.17 ml of 1 M methylene chloride solution; 1.17 mmol) After 0.5 hours of reaction at 0° C. the reaction mixture was washed with 1M TEAB aqueous solution. The organic solution was separated, dried over $Na_2SO_4$, and concentrated. The residue was purified by flash column chromatography, eluted with 1.5% $Et_3N/5\%$ $CH_3OH/CH_2Cl_2$. Fractions of the product were combined, washed with 1M TEAB aqueous solution, dried over $Na_2SO_4$, and concentrated, affording phosphorylated DMT-protected anthraquinone pseudonucleotide.

C. In a manner similar to that set forth in paragraphs A and B, the phosphorylated Mono DMT-protected ethyl, cholesteryl, TFA/DEA and TFA/DHED pseudonucleosides are prepared.

EXAMPLE 5

Synthesis of Oligomers Containing Pseudonucleosides

The phosphorylated pseudonucleosides of Example 4, and the CPG conjugated pseudonucleosides of Example 3, were then utilized in standard solid-phase oligomer synthesis techniques, as described in *Oligonucleotide Synthesis-A Practical Approach*, Gait, M. J., ed (1984) IRL Press, Ltd.

EXAMPLE 6

Synthesis of 5′-Cholesteryl-Oligomer-DHED/Rhodamine

Cholesterol Hydrogenphosphonate

Cholesterol (6.8 g; 7.6 mmol) in 50 ml of methylene chloride was added to a 0° C. solution of methylene chloride (90 ml) containing pyridine (3.2 ml, 40 mmol) and 2-chloro-4H-1,3,2-benzodioxyphosphorin-4-one (40 mmol). After a 1 hour reaction at 0° C., the reaction mixture was washed with 1 M tetraethyl ammonium bicarbonate (TEAB) aqueous solution twice. The organic phase was isolated, dried with sodium sulfate, evaporated, purified by flash column chromatography on silica gel, eluted with 10% methanol/2% Et₃N/methylene chloride. The combined product fractions were washed with 1 M TEAB aqueous solution, dried with sodium sulfate and evaporated to afford 4.88 g of product (50% yield).

Automated Oligomer Synthesis

Cholesterol hydrogenphosphonate was used in solid phase oligonucleotide synthesis utilizing standard solid-phase oligomer synthesis techniques, as described in *Oligonucleotide Synthesis - A Practical Approach*, Gait, M. J., ed. (1984) IRL Press, Ltd. Oligomer synthesis used TFA/DHED-coupled CPG and standard reagents, with the final step the addition of the cholesterol hydrogenphosphonate. Base protecting groups were removed in conc. ammonium hydroxide overnight at 45° C. (which also removes TFA from the DHED pseudonucleoside), desalted with a C8 Sepak column and DNA was eluted with 30% acetonitrile/water.

Conjugation of Oligonucleotide with 5-Carboxytetramethylrhodamine Succimidyl Ester The above 5′-cholesteryl oligonucleotide having the DHED residue in the 3′ position (100 O.D.), was dissolved in 50 μl sodium carbonate (pH 9.0) aqueous solution followed by addition, three times over a two hour period, of activated rhodamine (succinimidyl ester) (1 mg) in 20 ml 0.1 M aqueous sodium phosphate (pH 7.0). The reaction mixture was desalted by passing through a G-25 sephadex column. The cholesterol-oligonucleotiderhodamine conjugate was isolated by elution from a 20% polyacrylamide gel.

EXAMPLE 7

Properties of Oligomers Including Pseudonucleosides

The following oligomers were synthesized and tested for stability in vitro and in vivo, and specificity of hybridization to complementary DNA and RNA. The oligomers prepared are as follows, where "P" represents the pseudonucleotide residue.

| Oligomer No. | | |
|---|---|---|
| 1A | (Acridine) | 5′-CCC-TCT-CTT-TTT-CCP |
| 1C | (Anthraquinone) | |
| 2A | (Acridine) | 5′-CCC-TCT-PCT-TTT-TCC |
| 2C | (Anthraquinone) | |
| 3A | (Acridine) | 5′-CCC-TCT-CPT-TTT-TCC |
| 3C | (Anthraquinone) | |
| 4A | (Acridine) | 5′-PCC-CTC-TCT-TTT-TCC |
| 4C | (Anthraquinone) | |
| 5A | (Acridine) | 5′-CCC-TCT-PCT-TTT-TCC-P |
| 5C | (Anthraquinone) | |
| 6C | (Anthraquinone) | 5′-PCC-CTC-TCT-TTT-TCC-P |
| 7C | (Anthraquinone) | 5′-PCC-CTC-TPC-TTT-TTC-CP |
| Control | | 5′-CCC-TCT-CTT-TTT-CC |

Hydridization Stabilization

Table 1 gives the results with respect to stability of hybridization to complement as a difference in melting point, as compared to the control lacking the inclusion of the pseudonucleotide of the invention. As seen from the table, hybridization increased with respect to DNA and RNA complement in almost all cases.

TABLE 1

| | Δ T, °C. | |
|---|---|---|
| | DNA | RNA |
| 1A-Acridine | 5.5[a] | 4[b] |
| 1C-Anthraquinone | 5.5[c] | 4[d] |
| 2A-Acridine | 0[a] | −2.5[b] |
| 2C-Anthraquinone | 3.0[c] | −0.5[d] |
| 3A-Acridine | −3.0[a] | — |
| 3C-Anthraquinone | 2.5[c] | −0.5[d] |
| 4A-Acridine | 6.5[a] | 2.5[b] |
| 4C-Anthraquinone | 6.0[c] | 4.0[d] |
| 5A-Acridine | 2.0[a] | 0.5[b] |
| 5C-Anthraquinone | 8.5[c] | 4.0[d] |
| 6C-Anthraquinone | 9.5[c] | 8.0[d] |
| 7C-Anthraquinone | — | 8.0[d] |
| Control | 0 | 0 |

[a]~5 μM DNA/DNA (1/1) in 20 mM Tris/15 mM NaCl, pH 7.5 Tm of control was 41.5° C.
[b]~5 μM DNA/RNA (1/1) in 150 mM NaCl/50 mM Tris, pH 7.5 $T_m$ of control was 63.0° C.
[c]~5 μM DNA/DNA (1/1) in 150 mM NaCl/10 mM Na₂HPO₄ $T_m$ of control was 51.0° C.
[d]~1.6 μM DNA/RNA (1/1) in 150 mM NaCl/50 mM Tris, pH 7.5 $T_m$ of control was 60° C.

In a manner similar to that set forth in Examples 1–5 above, oligomers were constructed which include as "P*", the pseudonucleoside HO(CH₂)₆NH(CH₂)₆OH wherein the nitrogen is substituted with anthraquinone-i.e.,

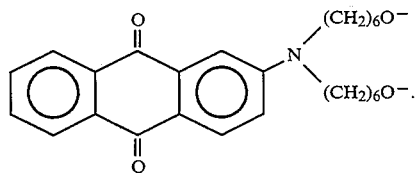

These analogs were tested for stability of hybridization with complementary RNA. The results, shown in Table 2, indicate the longer methylene chains in the pseudonucleoside do not result in enhanced stability as compared to the diethanolamine pseudonucleotides.

TABLE 2

| Oligomer | | Tm, °C. | Δ-T, °C. |
|---|---|---|---|
| 1* | 5′-CCC-TCT-CTT-TTT-CCP* | 64.0 | 4.0 |
| 2* | 5′-CCC-TCT-P*CT-TTT-TCC | 57.5 | −2.5 |
| 4* | 5′-P*CC-CTC-TCT-TTT-TCC | 63.5 | 3.5 |
| 5* | 5′-CCC-TCT-P*CT-TTT-TCC-P* | 58.5 | −1.5 |
| 6* | 5′-P*CC-CTC-TCT-TTT-TCC-P* | 65.0 | 5.0 |
| Control | 5′-CCC-TCT-CTT-TTT-CC | 60.0 | 0 |

Stability to Nuclease Degradation

The stability of the modified oligonucleotides to lysis was tested under conditions which simulate in vitro cell culture and typical in vivo environments. Oligomers were prepared, as described in Examples 1–5, of the sequences: 5'*TT-TTT-CTC-CAT-P wherein P represents diethanolamine pseudonucleoside derivatized respectively to Acridine (#A); Anthraquinone (#B); Ethyl (#C); Cholesterol (#D); TFA (#E); ETFA (#F); or not derivatized (#G). These oligomers were incorporated into oligonucleotides of the sequence: 5' TCC AGT GAT TTT TTT CTC CAT-P 3' which was internally-labeled by (i) ligation of the 5' 10-mer (5' TCC AGT GAT T 3') with the 3' 11-mer labelled with 32P* (5' *TT TTT CTC CAT-P), (ii) polyacrylamide gel electrophoresis to separate unligated 10-mer and 11-mer from the desired 21-met product (5' TCC AGT GAT T*TT TTT CTC CAT-P 3') and (iii) recovery of the 21-mer from the gel by overnight incubation in buffer.

The control uses the 3' labeled oligomer of the formula 5'*TT-TTT-CTC-CAT.

The 3'-modified oligonucleotides were treated with snake venom phosphodiesterase, under conditions where the control is completely degraded within 5 minutes. For all four modified oligomers, approximately 90% remained intact at 5 min, and 50% remained at 1 hr. No oligomer remained at 3 hr.

TABLE 3

| | Fetal Calf Serum | | | |
|---|---|---|---|---|
| | 0 days | 1 days | 3 days | 5 days |
| Control | 100% | 0% | 0% | 0% |
| A: Acridine | 100% | 80% | 20% | 10% |
| B: Cholesterol | 100% | 10 | 1% | 1% |
| C: Anthraquinone | 100% | 90% | 60% | 50% |
| D: Ethyl | 100% | 85% | 10% | 10% |

TABLE 4

| | Human Serum | | |
|---|---|---|---|
| | 0 hr | 4 hr | 18 hr |
| Control | 100% | 50% | 20% |
| A: Acridine | 100% | 90% | 80% |
| B: Cholesterol | 100% | 100% | 100% |

TABLE 5

| | Fetal Calf Serum | | | |
|---|---|---|---|---|
| | 0 | d1 | d3 | d5 |
| Control | 100% | 0% | 0% | 0% |
| A Acridine | 100% | 80% | 30% | 10% |
| B Cholesterol | 100% | 80% | 30% | 10% |
| C Anthraquinone | 100% | 80% | 50% | 40% |
| D Ethyl | 100% | 80% | 50% | 20% |
| E Underivatized Diethanolamine | 100% | 70% | 40% | 20% |
| F Rhodamine/DHED | 100% | 80% | 60% | 50% |

TABLE 6

| | Human Serum | | | |
|---|---|---|---|---|
| | 0 | d1 | d3 | d5 |
| Control | 100% | 0% | 0% | 0% |
| A Acridine | 100% | 70% | — | — |
| B Cholesterol | 100% | 90% | 90% | 90% |
| C Anthraquinone | 100% | 80% | 60% | 40% |
| D Ethyl | 100% | 80% | — | 30% |
| E Underivatized Diethanolamine | 100% | 90% | 60% | 40% |

TABLE 6-continued

| | Human Serum | | | |
|---|---|---|---|---|
| | 0 | d1 | d3 | d5 |
| F Rhodamine/DHED | 100% | 80% | 60% | 50% |

In comparison with control, all oligomers with the 3' hydroxyl modification by coupling to a pseudonucleoside showed enhanced stability, with significant oligomer remaining intact after 5 days for most of these compounds. The compounds were usually at least about 30% intact after 3 days in tissue culture medium.

Intracellular Stability

The fluorescent oligonucleotide 5' cholesteryl-TCC AGT GAT TTT TTT CTC CAT-DHED rhodamine-3' synthesized in Example 6 was used in this study. The oligonucleotide was added to Dulbeccos' modified Eagles' medium (DMEM) containing 10% heat inactivated fetal calf serum to give a concentration of 5 mM. The medium containing the fluorescent oligonucleotide was then added to mouse L cells and allowed to incubate for 2 h at 37° C. The cells were then washed six times in DMEM to remove extracellular oligonucleotide. The cells were then examined at different times by fluorescence microscopy to determine if the oligonucleotide remained intact or was degraded. Degradation of the oligonucleotide was monitored by following the loss of rhodamine from the cells. Free rhodamine diffuses out of the cells and rhodamine attached to oligonucleotide remains in the cells. Fluorescence intensities indicated that more than 60% of the oligonucleotide remained intact after three days of residence within the cells, showing that the 3' hydroxyl adduct rendered it stable to nuclease activity.

Specificity of Hybridization

Oligonucleotides which contain the diethanolamine pseudonucleoside coupled with anthraquinone at the beta-position of the anthraquinone ring system were also tested for the ability to retain specificity of hybridization with complementary or one basepair mismatched RNA under conditions of 150 mM NaCl/50 mM Tris. Table 7 shows that the oligonucleotide including the pseudonucleotide shows similar differentials with respect to completely matched or one basepair mismatched complement as do controls. As shown in Table 5, in a control experiment, not involving pseudonucleotides, the extension of the test oligomer by the addition of a thymidine nucleotide at the 5' end changes the melting temperature of the hybrid with complementary RNA by only 0.5° C. However, substitution of a single mismatch, as noted, lowers the melting temperature 8°. Similarly, when two anthraquinone-derivatized pseudonucleotides are included at the 5' and 3' ends, the lowering of the melting temperature caused by this single mismatch is 7.5°, comparable to the 8° previously obtained. Similarly, a single base pair mismatch at the 3' end effected a lowering of melting temperature in the control of 2.5°; a similar substitution in the oligomer further containing a pseudonucleotide at the 3' end resulted in a 4.5° melting point lowering as compared to the perfectly matched complement. This result demonstrates in the case of 3' mismatches the anthraquinone actually enhances specificity.

TABLE 7

| | $T_m$, °C. | $\Delta T$, °C. |
|---|---|---|
| Effect of Mismatch on Controls: | | |
| 5'-CCC-TCT-CTT-TTT-CC | 60.5 | — |
| 5'-T-CCC-TCT-CTT-TTT-CC | 61.0 | +0.5 |
| 5'-CCC-TCT-TTT-TTT-CC | 52.5 | −8.0 |
| Effect of Same Mismatch with Pseudonucleotide: | | |
| 5'-P-CCC-TCT-CTT-TTT-CC-P | 68.0 | — |
| 5'-P-CCC-TCT-TTT-TTT-CCP | 60.5 | −7.5 |

TABLE 7-continued

| | $T_m$, °C. | $\Delta T$, °C. |
|---|---|---|
| Effect of 3'-Terminal Mismatch on Control: | | |
| 5'-CCC-TCT-CTT-TTT-CC | 60.0 | — |
| 5'-CCC-TCT-CTT-TTT-CT | 57.5 | −2.5 |
| Effect of 3'-Terminal Mismatch with Pseudonucleotide: | | |
| 5'-CCC-TCT-CTT-TTT-CC-P | 64 | — |
| 5'-CCC-TCT-CTT-TTT-CT-P | 59.5 | −4.5 |

We claim:

1. A compound of the formula

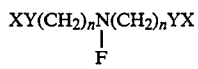

wherein n is an integer of 1 to 10;
each Y is independently O or S;
and wherein one X is selected from the group consisting of a nucleoside, a nucleotide, an oligonucleotide, an activated nucleotide synthesis coupling moiety and a solid support linked to Y and the other X is selected from the group consisting of H $PO_3^{2-}$, a protecting group, a nucleoside, a nucleotide, and an oligonucleotide; and
wherein F is a functional group capable of linking an additional moiety or a functional group and said additional moiety linked thereto, wherein said additional moiety is selected from the group consisting of a reporter group, an oligonucleotide cleavage entity, an oligonucleotide binding agent, a membrane penetration enhancer, an oligonucleotide crosslinking agent and a protecting group.

2. The compound of claim 1 wherein one X is a protecting group and the other X is an activated nucleotide synthesis coupling moiety.

3. The compound of claim 1 wherein one X is a protecting group or H and the other X is a solid support linked to Y.

4. The compound of claim 1 wherein F is a protecting group linked to N.

5. The compound of claim 4 wherein n is 2–6.

6. The compound of claim 1 wherein F is $-(CH_2)_{n'}Y'Pr$ wherein n' is 1–5, Y' is NH, O or S and Pr is a protecting group.

7. The compound of claim 1 wherein n is 2–6.

8. The compound of claim 7 wherein both Y are O.

9. The compound of claim 1 wherein F is selected from the group consisting of ethyl, cholesteryl, acridine, anthraquinone, and rhodamine linked to N.

* * * * *